United States Patent
Zhu et al.

(10) Patent No.: US 12,148,071 B2
(45) Date of Patent: Nov. 19, 2024

(54) METHODS AND APPARATUS FOR MRI RECONSTRUCTION AND DATA ACQUISITION

(71) Applicant: CHENGDU YIJIAN MEDICAL TECHNOLOGY CO., LTD, Chengdu (CN)

(72) Inventors: Ruixing Zhu, Chengdu (CN); Zhizun Zhang, Chengdu (CN); Hangxuan Li, Chengdu (CN)

(73) Assignee: HANGZHOU WEIYING MEDICAL TECHNOLOGY CO., LTD., Hangzhou (CN)

( * ) Notice: Subject to any disclaimer, the term of this patent is extended or adjusted under 35 U.S.C. 154(b) by 417 days.

(21) Appl. No.: 17/513,908

(22) Filed: Oct. 29, 2021

(65) Prior Publication Data

US 2022/0139003 A1     May 5, 2022

Related U.S. Application Data

(60) Provisional application No. 63/107,455, filed on Oct. 30, 2020.

(51) Int. Cl.
    *G06T 11/00*      (2006.01)
    *G06F 18/214*      (2023.01)
    *G06T 7/00*      (2017.01)

(52) U.S. Cl.
    CPC .......... *G06T 11/005* (2013.01); *G06F 18/214* (2023.01); *G06T 7/0014* (2013.01);
(Continued)

(58) Field of Classification Search
    CPC ................. G06T 11/005; G06T 7/0014; G06T 2207/10088; G06T 2207/20084;
(Continued)

(56) References Cited

U.S. PATENT DOCUMENTS 10,852,379 B2 * 12/2020 Chen ................. G01R 33/56509
2009/0128553 A1 * 5/2009 Perry .................... A61B 5/055
                                                             345/419

(Continued)

OTHER PUBLICATIONS

Wu et al, Quantitative assessment of the parallel MRI reconstruction using background noise uniformity, IEEE International Conference on Bioinformatics and Biomedicine (BIBM), pp. 400-404 (Year: 2015).*

(Continued)

*Primary Examiner* — Ping Y Hsieh
*Assistant Examiner* — Xiao Liu

(57) ABSTRACT

Methods and apparatus for MRI reconstruction and data acquisition are provided. The method for MRI reconstruction includes: obtaining MRI images and k-space training data and dividing into anatomical sections; training reconstruction models to predict MRI images from k-space data for individual anatomical sections; while scanning an object, identifying the anatomical sections by scout scans or navigator signals; selecting suitable reconstruction models; reconstructing anatomical sections using the selected models, and merging the images from anatomical sections. Reconstructed images obtained by the above methods and apparatus have better image quality such as lesser noise and artifacts, and less MRI data is needed for the same image quality.

14 Claims, 10 Drawing Sheets

(52) U.S. Cl.
CPC ........... *G06T 2207/10088* (2013.01); *G06T 2207/20084* (2013.01)

(58) Field of Classification Search
CPC ............ G06F 18/214; G01R 33/4818; G01R 33/4822; G01R 33/4824; G01R 33/4835; G01R 33/543; G01R 33/5608; A61B 6/00; G06V 10/774; G06V 10/82
See application file for complete search history.

(56) References Cited

U.S. PATENT DOCUMENTS

2010/0239143 A1* 9/2010 Griswold ............ G06F 18/2135
382/128
2020/0138382 A1* 5/2020 Cao ..................... G06T 7/0014
2020/0402204 A1* 12/2020 Huang ................. G06T 11/003

OTHER PUBLICATIONS

Frost et al, 3D Multi-Slab Diffusion-Weighted Readout-Segmented EPI with Real-Time Cardiac-Reordered k-Space Acquisition, Magnetic Resonance in Medicine 72:1565-1579 (Year: 2014).*

* cited by examiner

METHODS AND APPARATUS FOR MRI RECONSTRUCTION AND DATA ACQUISITION

CROSS REFERENCE TO RELATED APPLICATIONS

This application claims priority to U.S. Provisional Application No. 63/107,455, filed Oct. 30, 2020, which is hereby incorporated by reference herein as if set forth in its entirety.

BACKGROUND

1. Technical Field

The present disclosure relates to data processing technology, and particularly to a computer-implemented method for magnetic resonance imaging (MRI) reconstruction, a computer-implemented method for MRI data acquisition, and an apparatus for MRI reconstruction and data acquisition.

2. Description of Related Art

MRI is widely used for clinical diagnosis of various diseases. The raw data acquired by MRI scanners are k-space samples, which can be converted (i.e., reconstructed) to MRI images by reconstruction methods. The quality of MRI images is partially determined by the reconstruction methods, particularly when the k-space samples are undersampled to save the scan time.

Incorporating prior knowledge is known to improve image reconstruction. Existing reconstruction methods commonly uses prior knowledge such as receiver coil sensitivities (e.g. SENSE and GRAPPA) and transform-domain data sparsity (e.g. compressed sensing methods). However, one fact remains unexplored: human anatomical structures share great similarities between individuals and most clinical MRI scans are performed to image these anatomical structures in preset geometry views. For example, for brain MRI imaging, one commonly used view is the axial views where slices are planned parallel to the anterior commissure—posterior commissure line, covering whole brain from vertex to skull base. Therefore, the image reconstruction requires a lot of MRI data and there are more noise and artifacts in the reconstructed image.

BRIEF DESCRIPTION OF THE DRAWINGS

To describe the technical schemes in the embodiments of the present disclosure or in the prior art more clearly, the following briefly introduces the drawings required for describing the embodiments or the prior art. It should be understood that, the drawings in the following description merely show some embodiments of the present disclosure. For those skilled in the art, other drawings can be obtained according to the drawings without creative efforts.

DETAILED DESCRIPTION

In the following descriptions, for purposes of explanation instead of limitation, specific details such as particular system architecture and technique are set forth in order to provide a thorough understanding of embodiments of the present disclosure. However, it will be apparent to those skilled in the art that the present disclosure may be implemented in other embodiments that are less specific of these details. In other instances, detailed descriptions of well-known systems, devices, circuits, and methods are omitted so as not to obscure the description of the present disclosure with unnecessary detail.

For the purpose of describing the technical solutions of the present disclosure, the following describes through specific embodiments.

Figure 1:
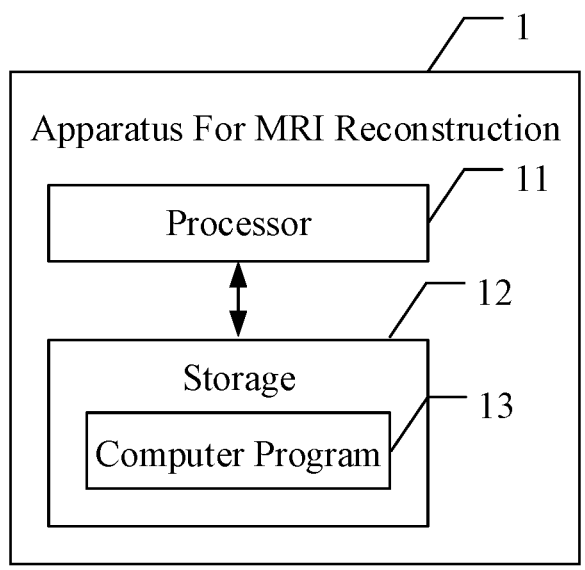
FIG. 1 is a schematic block diagram of an apparatus for MRI reconstruction and data acquisition according to an embodiment of the present disclosure.

FIG. 1 is a schematic block diagram of an apparatus for MRI reconstruction and data acquisition according to an embodiment of the present disclosure. The apparatus 1 is provided, which corresponds to a method for MRI reconstruction or/and a method for MRI data acquisition described in the following embodiments shown in FIG. 2-FIG. 9. In this embodiment, the apparatus 1 may be, for example, a desktop computer, a personal computer, a server, a mobile phone, a tablet, or a laptop computer, etc. As shown in FIG. 1, the apparatus 1 includes a processor 11, a storage 12, and a computer program 13 stored in the storage 12 and executable on the processor 11. When executing (instructions in) the computer program 13, the processor 11 implements the method for MRI reconstruction or/and the method for MRI data acquisition described in the following embodiments shown in FIG. 2-FIG. 9.

Exemplarily, the computer program 13 may be divided into one or more modules/units, and the one or more modules/units are stored in the storage 12 and executed by the processor 11 to realize the present disclosure. The one or more modules/units may be a series of computer program instruction sections capable of performing a specific function, and the instruction sections are for describing the execution process of the computer program 13 in the apparatus 1.

It can be understood by those skilled in the art that FIG. 1 is merely an example of the apparatus 1 and does not constitute a limitation on the apparatus 1, and may include more or fewer components than those shown in the figure, or a combination of some components or different components. For example, the apparatus 1 may further include an input/output device, a network access device, a bus, and the like.

The processor 11 may be a central processing unit (CPU), or be other general purpose processor, a digital signal processor (DSP), an application specific integrated circuit (ASIC), a field-programmable gate array (FPGA), or be other programmable logic device, a discrete gate, a transistor logic device, and a discrete hardware component. The general purpose processor may be a microprocessor, or the processor may also be any conventional processor.

The storage 12 may be an internal storage unit of the apparatus 1, for example, a hard disk or a memory of the apparatus 1. The storage 12 may also be an external storage device of the apparatus 1, for example, a plug-in hard disk, a smart media card (SMC), a secure digital (SD) card, flash card, and the like, which is equipped on the apparatus 1. Furthermore, the storage 12 may further include both an internal storage unit and an external storage device, of the apparatus 1. The storage 12 is configured to store the computer program 13 and other programs and data required by the apparatus 1. The storage 12 may also be used to temporarily store data that has been or will be output.

After research, the applicant found that with prior knowledge of anatomy, as well as the scan geometry information, the image contents at specific locations are largely predictable. This prior knowledge of anatomy and availability of large corresponding MRI image datasets can be used to develop new reconstruction methods for better MRI image quality, reconstructing from less or noisy raw MRI data.

The present disclosure aims to improve the reconstruction of MRI images by incorporating anatomical knowledge, which is learned by reconstruction models such as convolutional neural networks and generative adversarial networks. More specifically, training datasets comprising MRI images and corresponding k-space data are obtained from MRI scanners or by computer simulations, and divided into sections according to anatomy and possible MRI scan geometries. On each section, at least one reconstruction model is trained to predict the images from the k-space data. While scanning a subject, in addition to the main scans, at least one scout scan (a.k.a. localizer scan) is performed or navigator signals are collected. By matching the scout scan images (or navigator images) to the reference images of anatomical sections, related anatomical sections can be identified from the main scan data, and the main scan data are accordingly divided. The main scan data (including multi-slice 2D data, 3D volume, 2D or 3D dynamic volume data) are reconstructed on each section by the reconstruction models trained on or near this section, and the resulting images from sections are merged for storage, transmission or display.

Some aspects of the present disclosure have the following advantages: (1) the reconstructed images have better image quality such as lesser noise and artifacts; (2) less MRI data (i.e., less MRI scan time) is needed for the same image quality.

Figure 2:
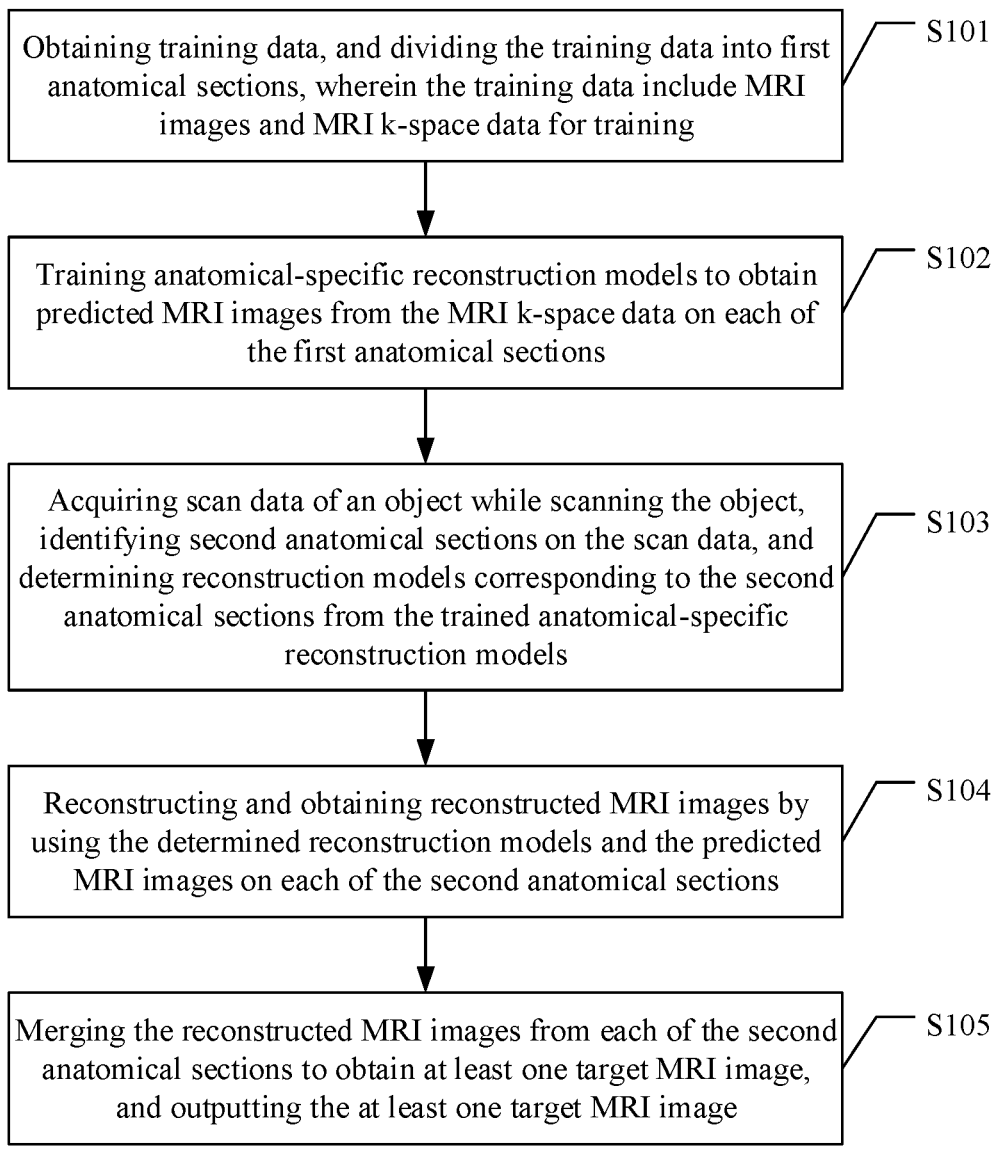
FIG. 2 is a flow chart of a computer-implemented method for MRI reconstruction according to an embodiment of the present disclosure.
Figure 10:
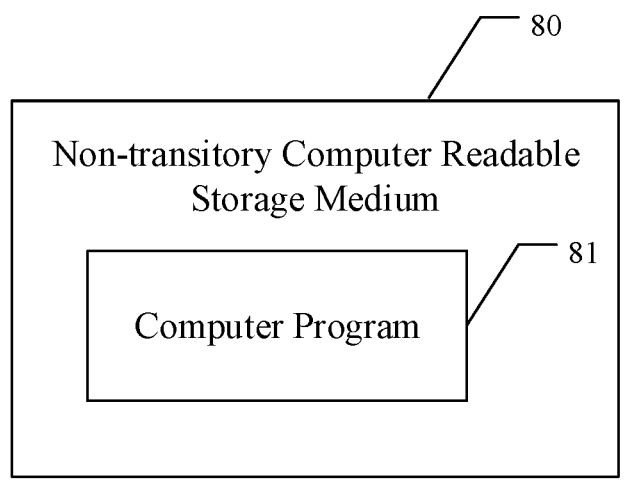
FIG. 10 is a schematic block diagram of a non-transitory computer readable storage medium according to an embodiment of the present disclosure.

FIG. 2 is a flow chart of a computer-implemented method for MRI reconstruction according to an embodiment of the present disclosure. The method is a computer-implemented method executable for a processor, which may be implemented through and applied to the apparatus for MRI data processing as shown in FIG. 1 or implemented through a non-transitory computer readable storage medium as shown in FIG. 10. The computer-implemented method for MRI reconstruction uses anatomical prior knowledge, and as shown in FIG. 2, in this embodiment, the method includes the following steps.

S101: obtaining training data, and dividing the training data into first anatomical sections, wherein the training data include MRI images and MRI k-space data for training;

S102: training anatomical-specific reconstruction models to obtain predicted MRI images from the MRI k-space data on each of the first anatomical sections;

S103: acquiring scan data of an object while scanning the object, identifying second anatomical sections on the scan data, and determining reconstruction models corresponding to the second anatomical sections from the trained anatomical-specific reconstruction models;

S104: reconstructing and obtaining reconstructed MRI images by using the determined reconstruction models and the predicted MRI images on each of the second anatomical sections; and S105: merging the reconstructed MRI images from each of the second anatomical sections to obtain at least one target MRI image, and outputting the at least one target MRI image.

The anatomical-specific reconstruction models are reconstruction models that can utilize the anatomical prior knowledge to reconstruct MRI images.

In some embodiments, the MRI k-space data for training are fully sampled or retrospectively undersampled.

In some embodiments, the MRI k-space data for training are two dimensional (2D) multi-slice data. Each of the first anatomical sections includes at least one slice. Each of the second anatomical sections includes at least one slice.

In some embodiments, the MRI k-space data for training are three dimensional (3D) multi-slab data, each of the first anatomical sections or each of the second anatomical sections comprises at least one slice.

In some embodiments, the sampling trajectory of the training data is Cartesian, or non-Cartesian (e.g. radial, spiral, stack-of-spirals, stack-of-stars).

In some embodiments, the MRI k-space data are 3D data with readout (kx) directions fully sampled. Each of the first anatomical sections includes at least one ky-kz plane perpendicular to the readout direction, and each of the second anatomical sections includes at least one ky-kz plane perpendicular to the readout direction.

In some embodiments, the training data are acquired from MRI scanners.

In some embodiments, the MRI k-space data are simulated from the MRI images for training.

In some embodiments, at least one or any combination of navigator signals, undersampled MRI data, and at least one scout scan is acquired and used to identify the second anatomical sections. For example, the at least one scout scan is acquired to identify the second anatomical sections, or the navigator signals are acquired to identify the second anatomical sections, or the undersampled MR data can be used to identify the second anatomical sections, or the aforementioned scout scan, navigator signals or undersampled MR data can be combined to identify the second anatomical sections.

In some embodiments, the anatomical-specific reconstruction models or the determined reconstruction models include artificial neural networks.

In some embodiments, the anatomical-specific reconstruction models are initially trained on all of the first anatomical sections.

In some embodiments, the anatomical-specific reconstruction models share the same weights for at least one layer.

In some embodiments, the anatomical-specific reconstruction models or the determined reconstruction models include a convolutional neural network (CNN).

In some embodiments, the anatomical-specific reconstruction models or the determined reconstruction models include a generative adversarial network (GAN).

In some embodiments, the anatomical-specific reconstruction models or the determined reconstruction models include an Auto-Encoder network.

In some embodiments, the anatomical-specific reconstruction models or the determined reconstruction models include other type of networks, modification, or combination of existing network architectures.

In some embodiments, the anatomical-specific reconstruction models are trained with MR data containing image abnormality or pathology so to improve the image reconstruction performance for dataset with pathology.

Figure 3A:
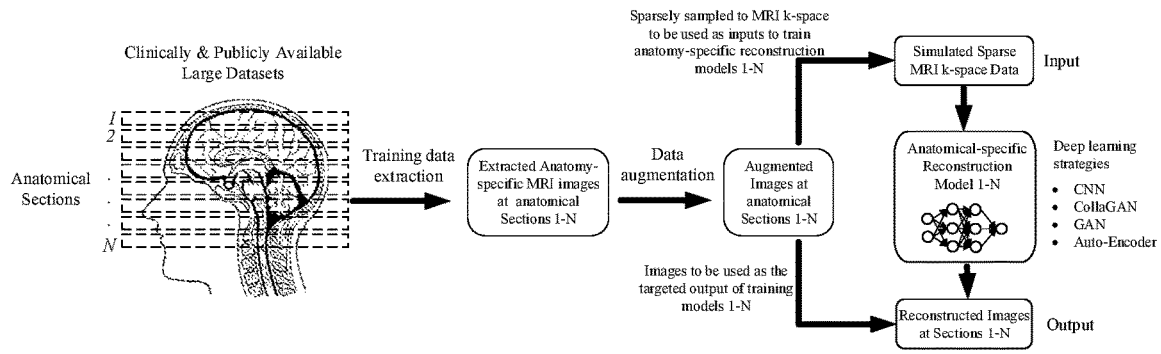
FIG. 3(A) and FIG. 3(B) are schematic diagrams of processes of incorporating anatomical information a priori into MRI image reconstruction through deep learning according to an embodiment of the present disclosure.
Figure 3B:
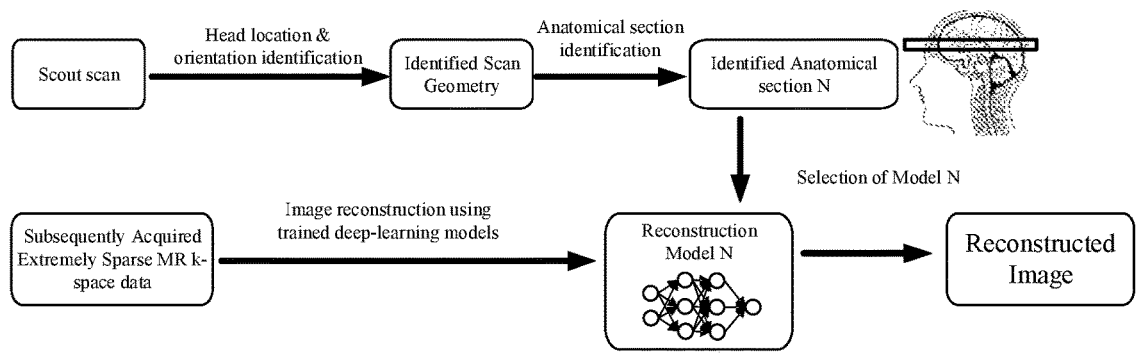

The following will be described in detail in connection with FIG. 3(A) to FIG. 8. FIG. 3(A) and FIG. 3(B) are schematic diagrams of processes of incorporating anatomical information a priori into MRI image reconstruction through deep learning according to an embodiment of the present disclosure.

FIG. 3(A) shows a process of training for anatomical specific model. Specifically, the training data including the MRI images and MRI k-space data for training from specific anatomical sections (1-N) are first extracted and used to train the models for image reconstruction of the sparse or noisy k-space data acquired from these sections. Different models (Model 1-N) will be trained for different imaging sections (1-N). This can be implemented with CNN, GAN, collaborative GAN (CollaGAN) and Auto-Encoder architectures. The specific anatomical sections refer to the imaging sections of the human body specified by the user's operation. The specific anatomical sections corresponds to the different scanned parts of the human body.

FIG. 3(B) shows a workflow of image reconstruction from sparse MR data. Specifically, at image reconstruction stage, the imaging/anatomical section can be first identified from the scout scan, and then used to select the corresponding reconstruction model. This strategy is expected to enable more effective image reconstruction from potentially lesser or/and noisier k-space data.

Figure 4:
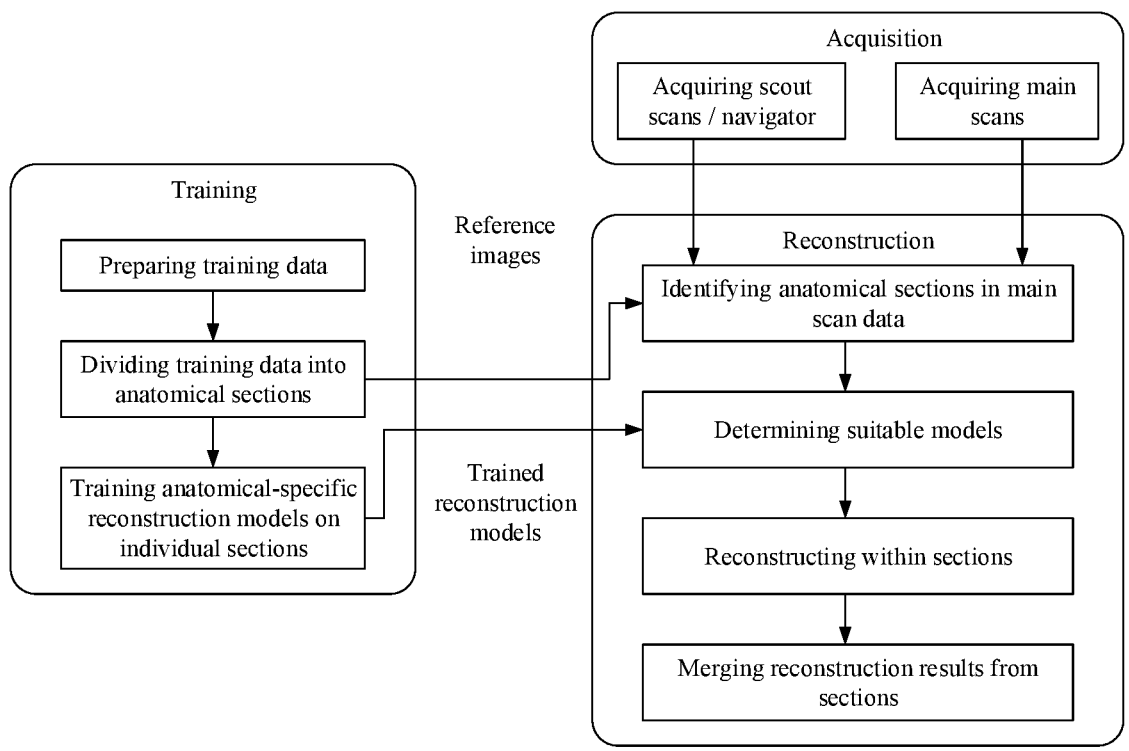
FIG. 4 is another flow chart of the computer-implemented method for MRI reconstruction according to an embodiment of the present disclosure.

FIG. 4 is another flow chart of the above computer-implemented method for MRI reconstruction according to an embodiment of the present disclosure. As shown in FIG. 4, for training of the above anatomical-specific reconstruction models, the training data are first prepared to include multiple pairs of MRI k-space data and MRI images (that is, the MRI images for training), then the training data are divided into sections (that is, the first anatomical sections) according to anatomy, and on each of the sections, the anatomical-specific reconstruction models are trained to predict MRI images (that is, the predicted MRI images is obtained) from the MRI k-space data. The predicted MRI images are also reconstructed MRI images. During the step of dividing the training data into the sections, at least one set of reference images are produced such that the anatomical sections can be located by the coordinates of the reference images. The trained reconstruction models and the coordinates of the anatomical sections are stored for later usage. When an object or a subject is positioned in the MRI scanner for imaging, scout scans or navigator signals are acquired, in addition to the main scans, to identify the anatomical sections (that is, the second anatomical sections) of the main scan data. On the identified anatomical sections of the main scan data, suitable reconstruction models (i.e., the models trained using the data from the corresponding anatomical sections) are selected to reconstruct the main scan data. The suitable reconstruction models are trained using the data from the corresponding anatomical sections. The models trained in this way learn the anatomical prior information, and embed such information into reconstruction for dedicated anatomical sections. The reconstructed images from individual sections are merged to form the output images.

Figure 5:
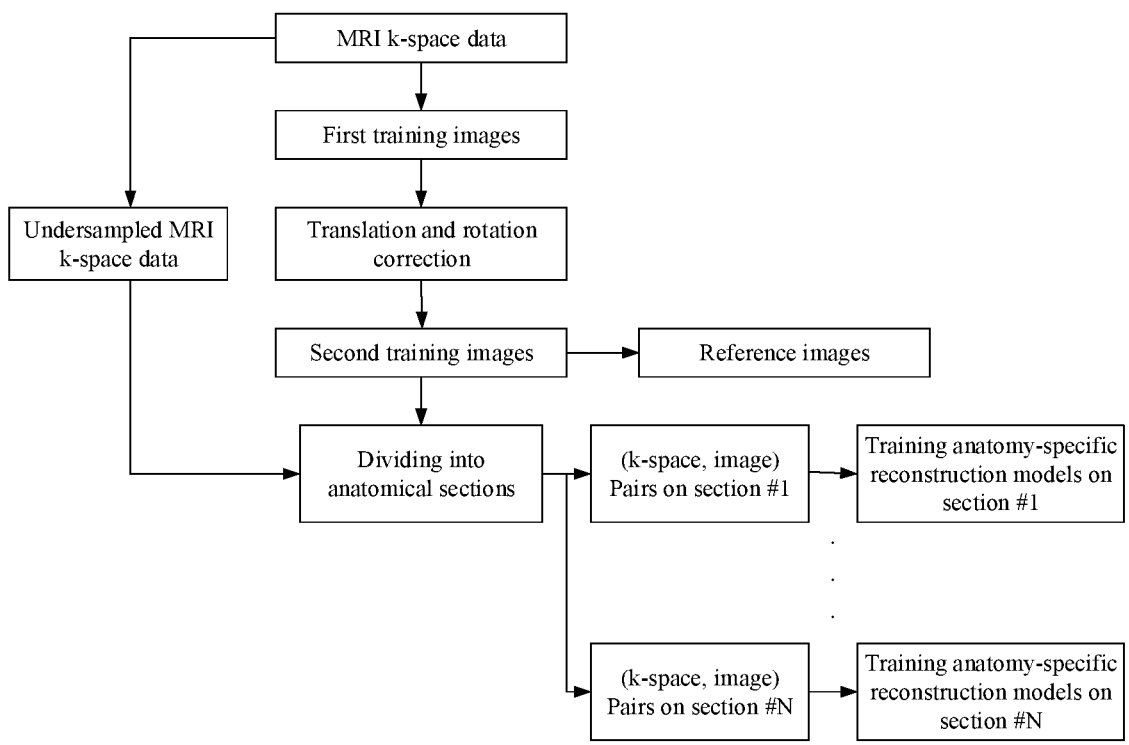
FIG. 5 is a schematic diagram of an embodiment of processes of training anatomical-specific reconstruction models in FIG. 2.

FIG. 5 illustrates the processes of training the above anatomical-specific reconstruction models in some embodiments. As shown in FIG. 5, the MRI k-space data are transformed to first training images, the geometry planning of which may vary. The difference of geometry planning of the first training images are corrected by translation and rotation correction algorithms such as mutual information minimization, forming second training images. In some embodiments, the second training images are averaged across scans to form the reference images. The second MRI images are sectioned to N parts according to anatomy. For example, every K millimeters from anterior to posterior (or superior to inferior, or left to right) forms one section. The MRI k-space data are also undersampled according to preset k-space trajectories, forming undersampled MRI k-space data. For every section, the MRI images and corresponding undersampled k-space data are organized into pairs and the reconstruction models are trained on these pairs using, for example, cross-entropy minimization, mean square error minimization or hinge loss minimization, to predict the images from the k-space data.

Figure 6:
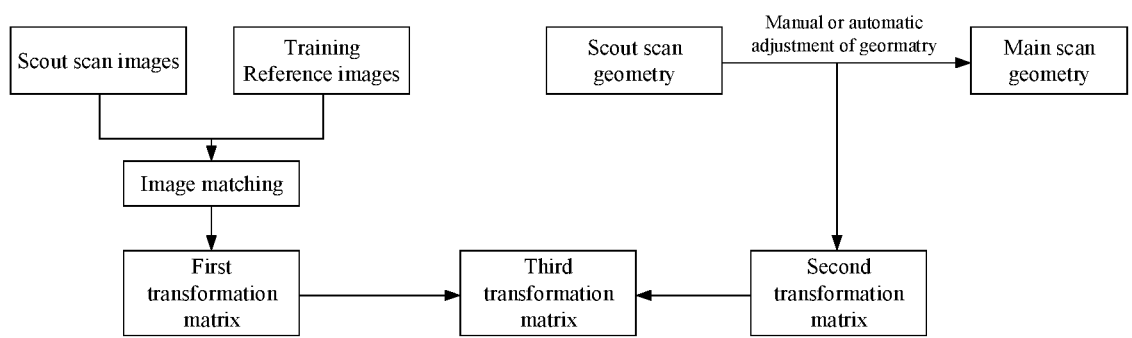
FIG. 6 is a schematic diagram of an embodiment of a method for identifying the second anatomical sections in FIG. 2 using scout scans.

FIG. 6 illustrates the method for identifying the above second anatomical sections using scout scans in some embodiments. In this embodiment, the scan data includes main scan data and scout scan data. The scan data is used to reconstruct images including the above reconstructed MRI images obtained based on the main scan data, and the scout images obtained based on the scout scan data. As shown in FIG. 6, first transformation matrices (affine transformation) from scout images obtained by the scout scans to the training reference images are obtained by image matching algorithms, such as mutual information minimization. Then second transformation matrices from the scout images to the main scans are obtained from the MRI scanner, as the geometry changes from scout images to the main scans are usually manually set by the operators or automatically adjusted by certain algorithms. The automatic adjustment can be implemented by identifying structural features in the scout images and used to for determining the positioning parameters. The automatic adjustment can also be implemented by registering the scout images to pre-defined template images, and use the image registration parameters to determine positioning parameters. Third transformation matrices are obtained by multiplying the first and second transformation matrices, which mapping the coordinates changes from the training reference images to the main scans. Then the anatomical sections defined previously on the training reference images are mapped onto the main scan images by converting the coordinates.

Figure 7:
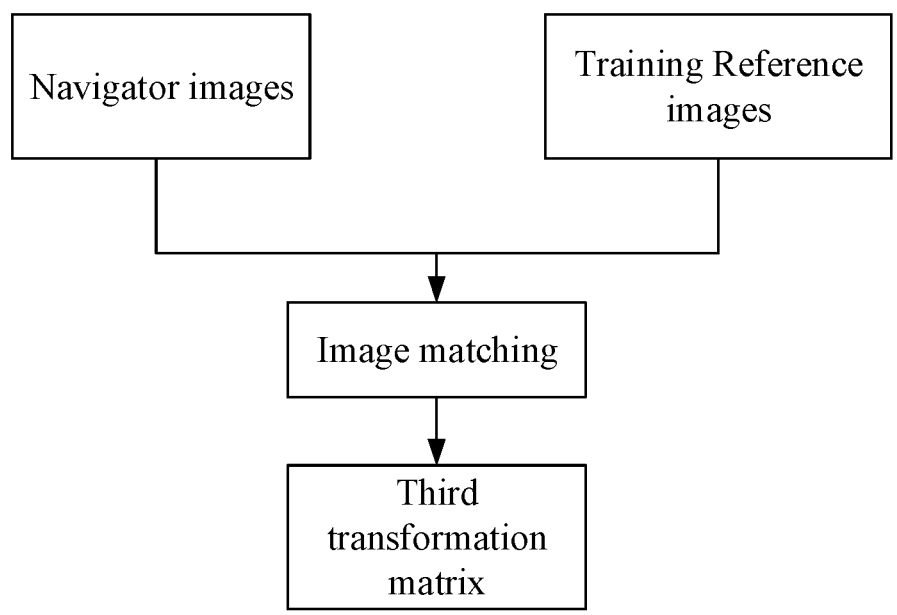
FIG. 7 is a schematic diagram of an embodiment of a method for identifying the second anatomical sections in FIG. 2 using navigator signals.

FIG. 7 illustrates the method for identifying the above second anatomical sections using navigator signals in some embodiments. As shown in FIG. 7 from the navigator signals, navigator images are obtained via Fourier transform. By image matching between the navigator images and the training reference images, third transformation matrices are obtained similarly to the aforementioned procedure using scout scans.

Figure 8:
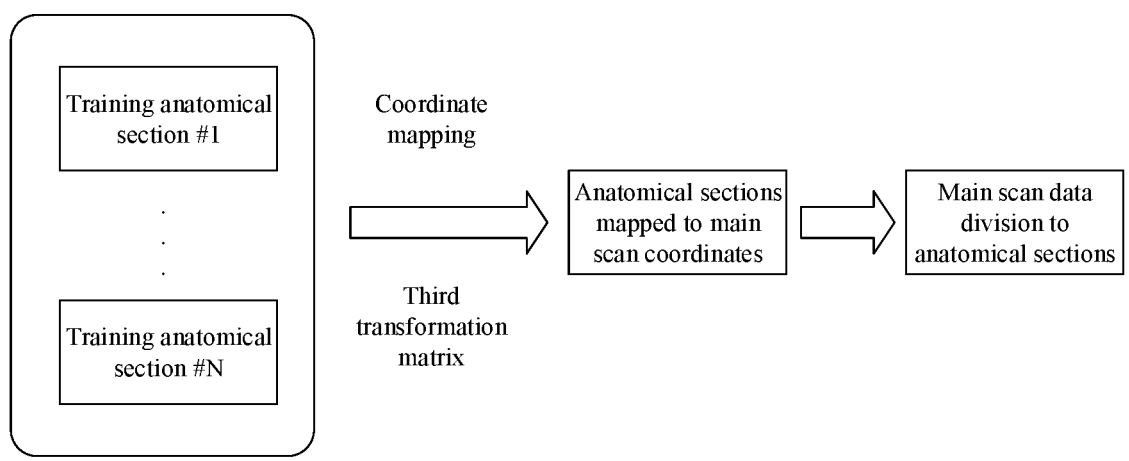
FIG. 8 is a flow chart of a method to divide main scan data into the second anatomical sections by transformation matrices according to an embodiment of the present disclosure.

FIG. 8 shows a method to divide main scan data into the second anatomical sections by (the above third) transformation matrices in some embodiments. As shown in FIG. 8, with the transformation matrices, the coordinates defining anatomical sections on training reference images are mapped to onto the main scan images. For individual sections, according to the coordinates on the main scan images, the corresponding part in main scan data are identified.

Figure 9:
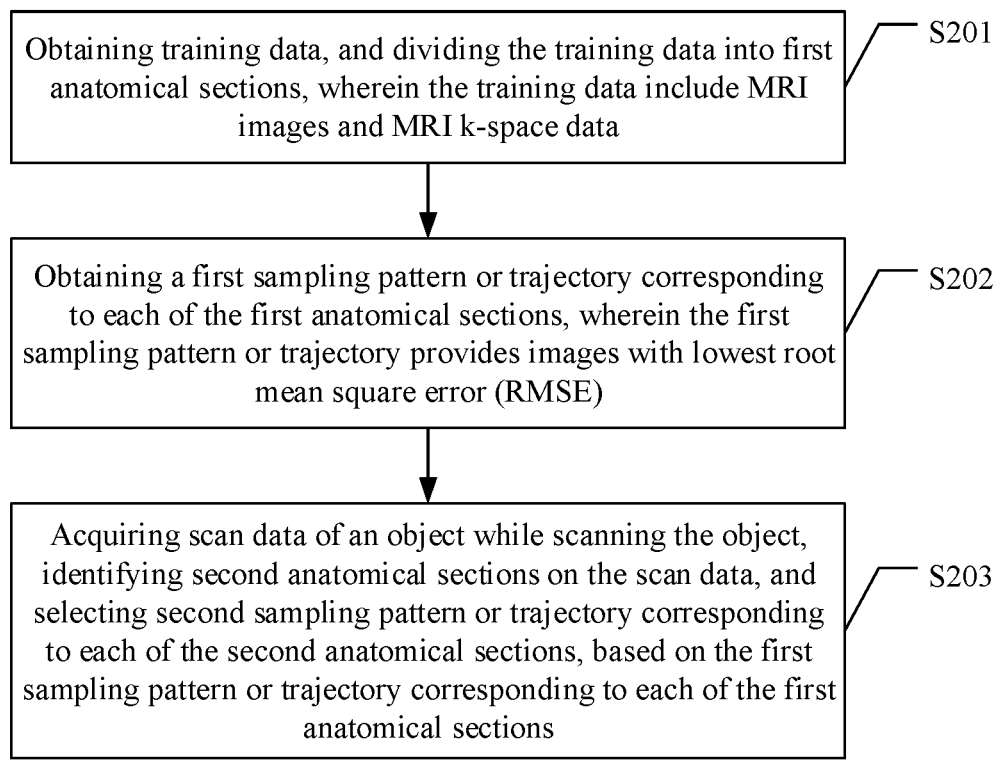
FIG. 9 is a flow chart of a computer-implemented method for MRI data acquisition according to an embodiment of the present disclosure.

FIG. 9 is a flow chart of a computer-implemented method for MRI data acquisition according to an embodiment of the present disclosure. The method is a computer-implemented method executable for a processor, which may be implemented through and applied to the apparatus for MRI data processing as shown in FIG. 1 or implemented through a non-transitory computer readable storage medium as shown in FIG. 10. In this embodiment, the method uses anatomical prior knowledge, and as shown in FIG. 9, the method includes the following steps.

S201: obtaining training data, and dividing the training data into first anatomical sections, wherein the training data include MRI images and MRI k-space data;

S202: obtaining a first sampling pattern or trajectory corresponding to each of the first anatomical sections, wherein the first sampling pattern or trajectory provides images with lowest root mean square error (RMSE); and S203: acquiring scan data of an object while scanning the object, identifying second anatomical sections on the scan data, and selecting second sampling pattern or trajectory corresponding to each of the second anatomical sections from the first sampling pattern or trajectory corresponding to each of the first anatomical sections.

In this embodiment, for example, the entire k-space is partially/sparsely filled during the MRI data acquisition process, so as to obtain the reconstructed images through image reconstruction algorithms, and the first and second sampling patterns or trajectories are used to indicate which locations in the k-space are sampled and the order of sampling process. The training data is acquired based on the first sampling pattern or trajectory corresponding to each of the first anatomical sections, and the scan data is acquired based on the second sampling pattern or trajectory corresponding to each of the second anatomical sections.

The anatomical sections include at least one of imaging sections, imaging slabs, and imaging regions.

In some embodiments, 2D multi-slice Cartesian/non-Cartesian acquisition is considered for each imaging section.

In some embodiments, 3D multi-slab Cartesian/non-Cartesian acquisition is considered for each imaging slab.

In some embodiments, 3D single-slab Cartesian/non-Cartesian acquisition is considered for each imaging region.

The above method for MRI reconstruction and the method for MRI data acquisition can refer to each other. The steps S201-S203 may also refer to the above description of the method in the embodiments shown in FIG. 2-FIG. 8. In some embodiments, the models of the above methods can be also trained with MRI data containing image abnormality or pathology so to improve the image reconstruction performance for dataset with pathology.

FIG. 10 is a schematic block diagram of a non-transitory computer readable storage medium according to an embodiment of the present disclosure. A non-transitory computer readable storage medium 80 is provided, which corresponds to the method for MRI reconstruction or/and the method for MRI data acquisition described in the above-mentioned embodiments. As shown in FIG. 8, the non-transitory computer readable storage medium 80 is configured to store a computer program 81. When the computer program 81 is executed by a processor, the method for MRI reconstruction or/and the method for MRI data acquisition in the above-mentioned embodiments is implemented.

The non-transitory computer readable storage medium 80 can be a server, a U disk, a mobile hard disk, a read-only memory (ROM), a random access memory (RAM), a magnetic disk, an optical disk, or other medium that can store program codes.

In the embodiments provided by the present disclosure, it should be understood that the disclosed method and apparatus (or device) may be implemented in other manners. For example, the above-mentioned apparatus embodiment is merely exemplary. For example, the division of modules or units is merely a logical functional division, and other division manner may be used in actual implementations, that is, multiple units or components may be combined or be integrated into another system, or some of the features may be ignored or not performed.

The units described as separate components may or may not be physically separated. The components represented as units may or may not be physical units, that is, may be located in one place or be distributed to multiple network units. Some or all of the units may be selected according to actual needs to achieve the objectives of this embodiment.

In addition, each of the functional units in each of the embodiments of the present disclosure can be integrated in one processing unit. Each unit can be physically exists alone, or two or more units can be integrated in one unit. The above-mentioned integrated unit can be implemented either in the form of hardware, or in the form of software functional units.

The integrated unit can be stored in a computer-readable storage medium if it is implemented in the form of a software functional unit and sold or utilized as a separate product. Based on this understanding, the technical solution of the present disclosure, either essentially or in part, contributes to the prior art, or all or a part of the technical solution can be embodied in the form of a software product. The software product is stored in a storage medium, which includes a number of instructions for enabling a computer device (which can be a personal computer, a server, a network device, etc.) or a processor to execute all or a part of the steps of the methods described in each of the embodiments of the present disclosure. The above-mentioned storage medium includes a variety of media such as a USB disk, a mobile hard disk, a read-only memory (ROM), a random access memory (RAM), a magnetic disk, and an optical disk which is capable of storing program codes.

As mentioned above, the forgoing embodiments are merely intended for describing but not for limiting the technical schemes of the present disclosure. Although the present disclosure is described in detail with reference to the above-mentioned embodiments, it should be understood by those skilled in the art that, the technical schemes in each of the above-mentioned embodiments may still be modified, or some of the technical features may be equivalently replaced, while these modifications or replacements do not make the essence of the corresponding technical schemes depart from the spirit and scope of the technical schemes of each of the embodiments of the present disclosure, and should be included within the scope of the present disclosure.

What is claimed is:

1. A computer-implemented method for magnetic resonance imaging (MRI) reconstruction, comprising executing on a processor with steps of:

obtaining training data, and dividing the training data into first anatomical sections, wherein the training data comprise MRI images and MRI k-space data for training;

training anatomical-specific reconstruction models to obtain predicted MRI images from the MRI k-space data on each of the first anatomical sections;

acquiring scan data of an object while scanning the object, identifying second anatomical sections on the scan data, and determining reconstruction models corresponding to the second anatomical sections from the trained anatomical-specific reconstruction models;

reconstructing and obtaining reconstructed MRI images by using the determined reconstruction models and the predicted MRI images on each of the second anatomical sections; and merging the reconstructed MRI images from each of the second anatomical sections to obtain at least one target MRI image, and outputting the at least one target MRI image;

wherein the MRI k-space data are three dimensional (3D) data with readout (kx) directions fully sampled, and each of the first anatomical sections and the second anatomical sections comprises at least one ky-kz plane perpendicular to a readout direction.

2. The method of claim 1, wherein a sampling trajectory of the training data is Cartesian, or non-Cartesian.

3. The method of claim 1, wherein the training data are acquired from MRI scanners.

4. The method of claim 1, wherein the MRI k-space data are simulated from the MRI images for training.

5. The method of claim 1, wherein at least one or any combination of navigator signals, undersampled MRI data, and at least one scout scan is acquired and used to identify the second anatomical sections.

6. The method of claim 1, wherein the anatomical-specific reconstruction models or the determined reconstruction models comprise artificial neural networks.

7. The method of claim 6, wherein the anatomical-specific reconstruction models are initially trained on all of the first anatomical sections.

8. The method of claim 6, wherein the anatomical-specific reconstruction models share same weights for at least one layer.

9. The method of claim 6, wherein the anatomical-specific reconstruction models or the determined reconstruction models comprise a convolutional neural network (CNN).

10. The method of claim 6, wherein the anatomical-specific reconstruction models or the determined reconstruction models comprise a generative adversarial network (GAN).

11. The method of claim 6, wherein the anatomical-specific reconstruction models or the determined reconstruction models comprise an Auto-Encoder network.

12. The methods of claim 1, wherein the anatomical-specific reconstruction models are trained with MR data containing image abnormality or pathology.

13. A computer-implemented method for MRI data acquisition, comprising executing on a processor with steps of:

obtaining training data, and dividing the training data into first anatomical sections, wherein the training data comprise MRI images and MRI k-space data;

obtaining a first sampling pattern or trajectory corresponding to each of the first anatomical sections, wherein the first sampling pattern or trajectory provides images with lowest root mean square error (RMSE); and acquiring scan data of an object while scanning the object, identifying second anatomical sections on the scan data, and selecting second sampling pattern or trajectory corresponding to each of the second anatomical sections from the first sampling pattern or trajectory corresponding to each of the first anatomical sections;

wherein the MRI k-space data are three dimensional (3D) data with readout (kx) directions fully sampled, and each of the first anatomical sections and the second anatomical sections comprises at least one ky-kz plane perpendicular to a readout direction.

14. An apparatus for MRI reconstruction and data acquisition, comprising:

a non-transitory storage;

a processor electronically coupled to the non-transitory storage; and a computer program stored in the non-transitory storage and executable by the processor, wherein the computer program comprises:

instructions for obtaining training data, and dividing the training data into first anatomical sections, wherein the training data comprise MRI images and MRI k-space data for training;

instructions for training anatomical-specific reconstruction models to obtain predicted MRI images from the MRI k-space data on each of the first anatomical sections;

instructions for acquiring scan data of an object while scanning the object, identifying second anatomical sections on the scan data, and determining reconstruction models corresponding to the second anatomical sections from the trained anatomical-specific reconstruction models;

instructions for reconstructing and obtaining reconstructed MRI images by using the determined reconstruction models and the predicted MRI images on each of the second anatomical sections; and instructions for merging the reconstructed MRI images from each of the second anatomical sections to obtain at least one target MRI image, and outputting the at least one target MRI image;

wherein the MRI k-space data are three dimensional (3D) data with readout (kx) directions fully sampled, and each of the first anatomical sections and the second anatomical sections comprises at least one ky-kz plane perpendicular to a readout direction.

\* \* \* \* \*